United States Patent [19]

Hayashi et al.

[11] 4,013,580

[45] Mar. 22, 1977

[54] METHOD OF PREVENTING FORMATION OF POPCORN CHLOROPRENE POLYMER

[75] Inventors: Takao Hayashi; Akihiko Shimizu, both of Shin-nanyo, Japan

[73] Assignee: Toyo Soda Manufacturing Co., Ltd., Yamaguchi, Japan

[22] Filed: May 21, 1975

[21] Appl. No.: 579,684

Related U.S. Application Data

[63] Continuation-in-part of Ser. No. 386,851, Aug. 8, 1973, abandoned.

[30] Foreign Application Priority Data

Aug. 9, 1972 Japan .............................. 47-79186

[52] U.S. Cl. .............................. 252/182; 252/403; 260/577; 260/652.5 P; 260/655

[51] Int. Cl.² ................. C07C 17/42; C07C 21/21; C07C 87/60

[58] Field of Search ........... 252/182, 403; 260/655, 260/652.5 P, 577

[56] References Cited

UNITED STATES PATENTS

| | | | |
|---|---|---|---|
| 3,042,726 | 7/1962 | Cook | 260/652.5 P |
| 3,151,161 | 9/1964 | Mullins | 260/577 |
| 3,275,531 | 9/1966 | Sennewald et al. | 260/655 |
| 3,576,877 | 4/1971 | Albert et al. | 260/577 |

OTHER PUBLICATIONS

D'Amico et al., "Nitrosoanilines," Jour. Am. Chem. Soc., vol. 81, Nov. 20, 1959, pp. 5957–5963.
Fieser & Fieser, "Textbook of Organic Chemistry," Heath & Co., 1950, p. 485.

Primary Examiner—Benjamin R. Padgett
Assistant Examiner—Irwin Gluck
Attorney, Agent, or Firm—Oblon, Fisher, Spivak, McClelland & Maier

[57] ABSTRACT

The formation of popcorn chloroprene polymer is prevented by adding an N-nitroso aniline compound of the formula

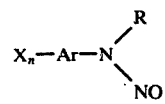

wherein Ar is a phenyl group; R represents a $C_{1-8}$ alkyl or a carboxymethyl group and when R is a $C_{1-8}$ alkyl group, X is a hydroxyl group and $n$ is 1 or 2; and when R is a carboxymethyl group, X is a halogen or hydroxyl group and $n$ is 0, 1 or 2.

5 Claims, No Drawings

METHOD OF PREVENTING FORMATION OF POPCORN CHLOROPRENE POLYMER

CROSS-REFERENCE TO RELATED APPLICATIONS

This application is a continuation-in-part of application Ser. No. 386,851, filed Aug. 8, 1973 now abandoned.

BACKGROUND OF THE INVENTION

1. Field of the Invention

The present invention relates to a method for preventing the formation of a popcorn chloroprene polymer.

1. Description of the Prior Art

Chloroprene monomer tends to undergo popcorn polymerization (otherwise known as ω-polymerization) whereby opaque granular solids are formed during storage of the monomer, or during a process step, such as distillation or the production of polymers from the monomer. Once the popcorn polymer forms, it tends to act unfavorably as nucleating site for the absorption and consequent consumption of chloroprene monomer. Once the formation of the popcorn polymer has started, it continues to grow at a very rapid rate and detrimentally acts to clog the process equipment. Because the popcorn polymer which forms is not soluble in solvents, its formation must be prevented.

Heretofore, in order to inhibit α- and μ-polymerization during the storage of chloroprene monomer or during the production of chloroprene polymers, it has been known to add a stabilizer such as phenothiazine and/or tertiary butylcatechol to the monomer. However, these inhibitors are ineffective in preventing ω-polymerization (popcorn polymerization) and β-polymerization of chloroprene monomer.

A need therefore exists for an inhibitor which effectively prevents ω-polymerization of chloroprene monomer.

SUMMARY OF THE INVENTION

Accordingly, one object of the present invention is to provide an inhibitor which effectively prevents ω-polymerization of chloroprene monomer from an industrial point of view.

Another object of the invention is to provide a series of aniline derivatives containing the N-nitroso group as an effective inhibitor for the prevention of formation of popcorn polymers.

Another object of the invention is to facilitate the removal of an inhibitor from chloroprene monomer containing the inhibitor by washing the monomer with an alkaline solution, thereby eliminating the heretofore conventional distillation procedure.

Briefly, these objects and other objects of the invention as hereinafter will become more readily apparent can be attained by providing an inhibitor for the prevention of popcorn chloroprene polymers which comprises an N-nitroso aniline compound having the formula

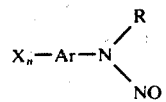

wherein Ar is a phenyl group; R represents a $C_{1-8}$ alkyl or a carboxymethyl group and when R is a $C_{1-8}$ alkyl group, X is hydroxyl group and $n$ is 1 or 2; and when R is a carboxymethyl group, X is a halogen or hydroxyl group and $n$ is 0, 1 or 2.

DETAILED DESCRIPTION OF THE PREFERRED EMBODIMENTS

Suitable N-nitroso aniline compounds which function as effective inhibitors for the prevention of popcorn chloroprene polymers include N-nitroso-N-methyl-p-hydroxyaniline; N-nitroso-N-methyl-m,p-dihydroxyaniline; N-nitroso-N-butyl-p-hydroxyaniline; N-nitroso-N-octyl-m,m-dihydroxyaniline; N-nitroso-N-phenylglycine; N-nitroso-N-p-chlorophenylglycine and N-nitroso-n-p-hydroxyphenylglycine. The N-nitroso compounds can be used alone or in combination with tertiary butylcatechol. Since these nitroso compounds are soluble in the chloroprene monomer, the concentration of the compounds in chloroprene can be kept constant.

The quantity of the inhibitor used in the present invention depends upon the temperature of the chloroprene monomer system, the operation time and other conditions. Usually from 0.001 to 0.1 part by weight, preferably from 0.01 to 0.03 parts by weight of the inhibitor is used per 100 parts by weight of the chloroprene monomer. The chloroprene monomer system can contain an inert solvent such as an aliphatic or aromatic hydrocarbon. The chloroprene monomer system can also contain a comonomer such as butadiene, isoprene, styrene, 2,3-dichlorobutadiene, acrylate, methacrylate and acrylonitrile.

Another unexpectedly beneficial property of the inhibitor of the present invention is that it not only prevents popcorn chloroprene polymer formation, but it also can completely prevent the formation of other methanol insoluble polymers.

The manner in which the inhibitor of the invention is used is not critical. For example, as one step of the synthesis of chloroprene monomer, if the chloroprene monomer is distilled, a solution of the chloroprene monomer containing the inhibitor may be continuously fed into the column from the top in quantities, such that the concentration of the inhibitor in the chloroprene monomer present in the column, ranges from 0.01 to 0.03 parts by weight per 100 parts by weight of the chloroprene monomer. The inhibitor remaining at the bottom of the distillation column is removed therefrom, while the chloroprene monomer which has distilled from the column is obtained in high purity. During the distillation, no popcorn polymer will be formed.

Chloroprene monomer has a high degree of polymerizability and often the addition of a polymerization inhibitor is required for storage. The inhibitor of this invention is quite effective for this purpose. Chloroprene monomer can be stored by the addition of 0.01 to 0.03 parts by weight of the inhibitor to 100 parts by weight of the chloroprene monomer. When polymerization is desired, the inhibitor must first be removed.

In order to remove the conventional nitroso compounds such as N-nitroso-diphenylamine, distillation is applied. However, distillation has many disadvantages from the viewpoint of economics and required time for the removal. The inhibitors of this invention are soluble in alkaline aqueous solutions so that they can easily be removed by washing the chloroprene monomer containing the inhibitor with an alkaline aqueous solution.

In this process, the chloroprene monomer containing the inhibitor is mixed with an alkaline aqueous solution with stirring. The mixture is permitted to stand until an upper phase of chloroprene monomer and a lower phase of an alkaline aqueous solution containing the inhibitor is formed. The alkaline aqueous solutions used in the invention can be an aqueous solution of an alkali metal hydroxide, such as sodium hydroxide and potassium hydroxide. The concentration of the alkali metal hydroxide is usually in a range of 0.005 to 20 wt%, preferably 1 to 10 wt%. The ratio of the alkali aqueous solution to the chloroprene containing the inhibitor should be in the range of 0.1 to 10, preferably 0.5 to 3 by volume. The time for stirring is usually 5 to 60 minutes. The number of washings is not critical and is usually in the range of 1 to 5 times. It is preferable to wash twice or more in order to remove substantially all of the inhibitor.

Having generally described this invention, a further understanding can be obtained by reference to certain specific examples which are provided herein for purposes of illustration only are not intended to be limiting unless otherwise specified.

COMPARATIVE EXAMPLE 1

A container was filled with 100 parts by weight of chloroprene monomer and with 0.2 parts by weight of tertiary butylcatechol, and then was sealed under a nitrogen stream. The container was then placed in a vessel at a constant temperature of 40° C. It was found that the conversion of chloroprene monomer by polymerization in the liquid phase was 2% and 3% after 15 days and 20 days, respectively.

EXAMPLE 1

The same test was conducted as described in Comparative example 1 except that 0.03 parts by weight of N-nitroso-N-methyl-p-hydroxyaniline was used instead of tertiary butylcatechol. No polymer was found in the solution after 30 days had passed.

EXAMPLE 2

The same test was conducted as described in Comparative Example 1 except that 0.1 parts by weight of tertiary butylcatechol and 0.01 part by weight of N-nitroso-N-methyl-p-hydroxyaniline were employed. No polymer was found in the solution after 30 days had passed.

EXAMPLE 3

The same test was conducted as described in Comparative Example 1 except that 0.1 part by weight of tertiary butylcatechol and 0.01 part by weight of N-nitroso-N-methyl-m,m-dihydroxyaniline was used instead of tert butylcatechol. No polymer was found in the solution after 30 days had passed.

EXAMPLE 4

The same test was conducted as described in Comparative Example 1 except that 0.03 part by weight of n-nitroso-N-phenylglycine was used instead of tertiary butylcatechol. No polymer in the solution was found after 30 days had passed.

EXAMPLE 5

The same test was conducted as described in Comparative Example 1 except that 0.1 part by weight of tertiary butylcatechol and 0.01 part by weight of N-nitroso-N-phenylglycine was used instead of tert butylcatechol alone. No polymer was found in the solution after 30 days had passed.

COMPARATIVE EXAMPLE 2

A container was filled with 100 parts by weight of chloroprene monomer with 0.03 part by weight of N-nitroso-diphenylamine. A 200 parts by weight of 10wt % aqueous solution of sodium hydroxide was added to the mixture and the mixture was stirred for 1 hour and was permitted to stand. The chloroprene monomer separated at the upper phase was removed. Though 100 wt parts of the chloroprene mononer and 100 wt parts of water were emulsified with 3.0 wt parts of potassium salt of rosin acid, and then 0.5 wt part of potassium persulfate was added to the mixture and a polymerization was conducted at 40° C for 4 hours, no polymer of chloroprene was obtained.

EXAMPLE 6

100 wt parts of 10% aqueous solution of sodium hydroxide was added to 10 wt parts of the chloroprene monomer containing 0.03 wt part of N-nitroso-N-methyl-p-hydroxyaniline and the mixture was stirred for 30 minutes. The same test was conducted as described in Comparative Example 2, except that after 3 hours, chloroprene was polymerized to a conversion of 70% because of removal of the inhibitor.

EXAMPLE 7

A 100 wt parts of chloroprene monomer containing 0.1 wt part of t-butylcatechol and 0.01 of N-nitroso-n-methyl-p-hydroxyaniline was washed with 70 wt parts of 3 wt% aqueous solution of potassium hydroxide twice while stirring for 30 minutes and chloroprene monomer was separated. The same test was conducted as described in Comparative Example 2, except using the chloroprene monomer. After 3 hours, chloroprene was polymerized to a conversion degree of 70%.

EXAMPLE 8

A 100 wt part of chloroprene monomer containing 0.03 wt part of N-nitroso-phenylglycine was washed with 50 wt parts of 3 wt% aqueous solution of sodium hydroxide three times while stirring for 15 minutes and chloroprene monomer was separated. The same test was conducted as described in Comparative Example 2 except using the chloroprene monomer. After 3 hours, chloroprene was polymerized to a conversion degree of 70%.

Having now fully described this invention, it will be apparent to one of ordinary skill in the art that many changes and modifications can be made thereto without departing from the spirit or scope of the invention as set forth herein.

What is to be claimed as new and intended to be covered by Letters Patent is:

1. A method for preventing the formation of popcorn chloroprene polymer, which comprises:

adding an N-nitroso aniline compound having the formula

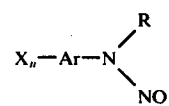

wherein Ar is a phenyl group; R represents a $C_{1-8}$ alkyl or a carboxymethyl group and when R is $C_{1-8}$ alkyl, X is hydroxyl and $n$ is 1 or 2; and when R is carboxymethyl group, X is halogen or hydroxyl and $n$ is 0,1 or 2, to chloroprene monomer, wherein said N-nitrosoaniline is easily removed from said chloroprene monomer by washing the same with an aqueous alkaline solution.

2. The method of claim 1, wherein 0.001 – 0.1 part by weight of said N-nitroso aniline compound is added to 100 parts by weight of said chloroprene monomer.

3. The method of claim 1, wherein said chloroprene monomer contains an inert solvent.

4. The method of claim 1, wherein said chloroprene monomer contains a comonomer of butadiene, isoprene, styrene, 2,3-dichlorobutadiene, acrylate, methacrylate or acrylonitrile.

5. The method of claim 1, wherein said N-nitroso aniline compound is selected from the group consisting of N-nitroso-N-methyl-p-hydroxyaniline; N-nitroso-N-methyl-m,p-dihydroxyaniline; N-nitroso-N-butyl-p-hydroxyaniline; N-nitroso-N-octyl-m,m-dihydroxyaniline; N-nitroso-N-phenylglycine; N-nitroso-N-p-chlorophenylglycine; and N-nitroso-N-p-hydroxyphenylglycine.

* * * * *